(12) United States Patent
Groenendaal et al.

(10) Patent No.: US 6,852,830 B2
(45) Date of Patent: Feb. 8, 2005

(54) 3,4-ALKYLENEDIOXYTHIOPHENE COMPOUNDS AND POLYMERS THEREOF

(75) Inventors: Bert Groenendaal, Sinaai (BE); Frank Louwet, Diepenbeek (BE)

(73) Assignee: Agfa-Gevaert, Mortsel (BE)

( * ) Notice: Subject to any disclaimer, the term of this patent is extended or adjusted under 35 U.S.C. 154(b) by 49 days.

(21) Appl. No.: 10/319,976

(22) Filed: Dec. 16, 2002

(65) Prior Publication Data

US 2003/0176628 A1 Sep. 18, 2003

Related U.S. Application Data

(60) Provisional application No. 60/349,523, filed on Jan. 18, 2002.

(30) Foreign Application Priority Data

Dec. 20, 2001 (EP) ............................. 01000781

(51) Int. Cl.[7] .......................... C08G 75/00; C08G 65/34
(52) U.S. Cl. ...................... 528/373; 528/377; 528/425; 528/480; 526/256
(58) Field of Search ................................. 528/373, 377, 528/425, 480; 526/256

(56) References Cited

U.S. PATENT DOCUMENTS 5,111,327 A 5/1992 Blohm et al.
6,635,729 B1 10/2003 Groenendaal et al.

OTHER PUBLICATIONS

Groenendaal et al; "Poly (3,4–ethylenedioxythiophene) and its Derivatives: Past, Present, and Future," *Advanced Materials*, vol. 12 (7), 481–494 (Apr. 4, 2000).

McCullough et al; "Self–Assembly and Disassembly of Regioregular, Water Soluble Polythiophenes: Chemoselective Ionchromatic Sensing in Water," *J. Am. Chem. Soc.*, vol. 119, 633–634 (1997).
EP Search Report 01 00 0781 (May 24, 2002).

*Primary Examiner*—Duc Truong
(74) *Attorney, Agent, or Firm*—Leydig, Voit & Mayer Ltd.

(57) ABSTRACT

A thiophene compound represented by formula (I):

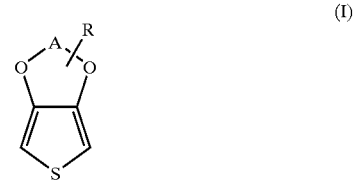

in which A represents a $C_{1-5}$-alkylene bridge; R represents a $—R^1—(C=O)—R^2$ group; $—R^1—$ represents a $—R^3—$ or $—R^4—X—R^5—$ group; $R^2$ is hydrogen, a hydroxy group, a thiol group, $—NR^6R^7$, $—OR^8$ or a $—SR^9$ group; $R^3$, $R^4$ and $R^5$ are independently an alkylene group or an arylene group; X is a $—O—$, $—S—$ or $=NR^{10}$; $R^6$ and $R^7$ are independently hydrogen, an optionally substituted amino group or an optionally substituted alkyl group; $R^8$ and $R^9$ are independently an optionally substituted alkyl group (optionally with at least one substituent selected from the group consisting of an alcohol, amide, ether, ester or sulfonate group), an optionally substituted aryl group or a $—SiR^{11}R^{12}R^{13}$ group; $R^{10}$ is an alkyl, aryl or acyl group; and $R^{11}$, $R^{12}$ and $R^{13}$ are independently an optionally substituted alkoxy or alkyl group; polymers derived therefrom; a process for polymerizing a thiophene according to formula (I), optionally chemically or electrochemically; and solutions, dispersions, pastes and layers containing polymers derived therefrom.

15 Claims, No Drawings

3,4-ALKYLENEDIOXYTHIOPHENE COMPOUNDS AND POLYMERS THEREOF

The application claims the benefit of U.S. Provisional Application No. 60/349,523 filed Jan. 18, 2002, which is incorporated by reference.

FIELD OF THE INVENTION

The present invention relates to new 3,4-alkylenedioxythiophene compounds and polymers thereof.

BACKGROUND OF THE INVENTION

Numerous polythiophenes have been studied extensively due to their interesting electrical and/or optical properties. Polythiophenes become electrically conducting upon chemical or electrochemical oxidation or reduction.

EP-A 257 573 discloses an intrinsically electrically conductive polymer, wherein through connection in the 2-position and/or the 5-position are coupled to one another, statistically averaged from 60 to 100% by weight structural units, which are derived from at least one monomer of the formula (1):

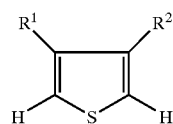

(1)

in which $R^1$ is a C1–C2-alkoxy group or —O(CH$_2$CH$_2$O)$_n$CH$_3$ with n=1 to 4 and $R^2$ is a hydrogen atom, a $C_{1-12}$-alkyl group, a $C_{1-12}$-alkoxy group or —O(CH$_2$CH$_2$O)$_n$CH$_3$ with n=1 to 4, or $R^1$ and $R^2$ together are —O(CH$_2$)$_m$—CH$_2$— or —O(CH$_2$)$_m$—O— with m=1 to 12, 0 to 40% by weight structural units, which are derived from at least one monomer of the formula (2):

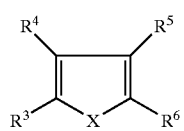

(2)

wherein $R^4$ and $R^5$ are independently of one another a hydrogen atom, a halogen atom, a $C_{1-12}$-alkyl group or aryl or together with C-atoms connected to them form an aromatic ring, $R^3$ and $R^6$ independently of one another represent a hydrogen atom or $R^3$ together with $R^4$ and the C-atoms connected to them or $R^5$ together with $R^6$ and the C-atoms connected to them each form an aromatic ring, X represents an oxygen atom, a sulfur atom, a =NH group, a =N-alkyl group or a =N-aryl group, 0 to 40% by weight structural units, which are derived from at least one monomer of formula (3):

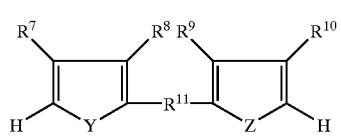

(3)

where $R^7$, $R^8$, $R^9$ and $R^{10}$ independently of one another represent a hydrogen atom, a $C_{1-12}$-alkyl group, a $C_{1-12}$-alkoxy group or an aryl group, Y and Z independently of one another represent an oxygen atom, a sulfur atom, a =NH group, a =N-alkyl group or a =N-aryl group, $R^{11}$ represents an arylene group, a heteroarylene group or a conjugated system of the formula (CH=CH)$_o$, wherein o is 1, 2 or 3, 0 to 40% by weight structural units, which are derived from at least one monomer of formula (4):

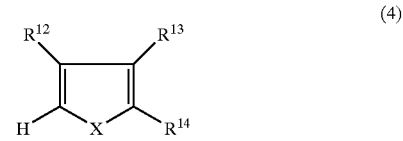

(4)

wherein $R^{12}$ and $R^{13}$ independently of one another represent a hydrogen atom, a halogen atom, a $C_{1-12}$-alkyl group, a $C_{1-12}$-alkoxy group, a $C_{1-4}$-alkylamino group or a $C_{1-4}$-acylamino group, $R^{14}$ represents a halogen atom, a $C_{1-12}$-alkyl group, a $C_{1-12}$-alkoxy group, a $C_{1-4}$-alkylamino group or a $C_{1-4}$-acylamino group and X has the meaning given above, wherein the polymer in the oxidized form is completely soluble in dipolar aprotic solvents at 25° C. and solutions with a content of at least 0.1 g of the polymer in 100 mL solvent at 25° C. are obtained.

EP-A 339 340 discloses a polythiophene containing structural units of the formula:

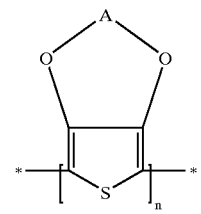

in which A denotes an optionally substituted $C_{1-4}$-alkylene radical and its preparation by oxidative polymerization of the corresponding thiophene.

EP-A 440 957 discloses dispersions of polythiophenes, constructed from structural units of formula (I):

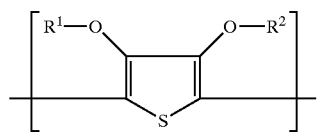

in which $R^1$ and $R^2$ independently of one another represent hydrogen or a $C_{1-4}$-alkyl group or together form an optionally substituted $C_{1-4}$-alkylene residue, in the presence of polyanions.

U.S. Pat. No. 5,111,327 discloses an electro-responsive polymer comprising chemically combined repeat units selected from the class consisting of,

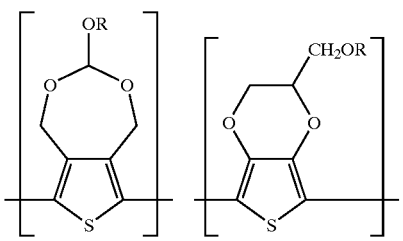

and a mixture thereof where R is a member selected from hydrogen or a $C_{(1-18)}$ organic radical. Examples 5, 10 and 15 disclose monomers and polymers where R is —CO(CH$_2$)$_2$—COOH.

Stereoregular carboxylic acid-functionalized polythiophenes have been reported by McCullough et al. in 1997 in Journal of the American Chemical Society, volume 119, page 84 and Synthetic Metals, volume 84, page 311. Irregular carboxylic acid-functionalized polythiophenes have been reported in 1990 by Bauerle et al. in Advanced Materials, volume 2, page 490, in 1996 by Englebienne et al. in Journal of the Chemical Society, Chemical Communications, page 1651 and by Masuda et al. in Makromol. Chem., Rapid Communications, volume 13, page 461. Poly(3-(2-(methacryloyl)ethylthiophene was reported by Lowe et al. in 1995 in Macromolecules, volume 28, page 4608.

For a recent overview of the chemistry and properties of poly(3,4-alkylenedioxythiophene) derivatives, see Groenendaal et al. in 2000 in Advanced Materials, volume 12, pages 481–494.

A general drawback of conductive polymers which have been prepared and studied up to now, is that their conductivities are still too low for certain applications, their visible light transmittances are insufficiently high and/or they are not processable.

OBJECTS OF THE INVENTION

It is therefore an aspect of the present invention to provide new 3,4-alkylenedioxythiophenes.

It is therefore another aspect of the present invention to provide polymers of the new 3,4-alkylenedioxythiophenes which exhibit high electrical conductivities and high visible light transmittances.

Further aspects and advantages of the invention will become apparent from the description hereinafter.

SUMMARY OF THE INVENTION

Aspects of the present invention are realized with a thiophene compound represented by formula (I):

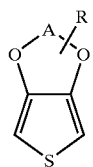

(I)

in which A represents a $C_{1-5}$-alkylene bridge; R represents a —R$^1$—(C=O)—R$^2$ group; —R$^1$— represents a —R$^3$— or —R$^4$—X—R$^5$— group; R$^2$ is hydrogen, a hydroxy group, a thiol group, —NR$^6$R$^7$, —OR$^8$ or a —SR$^9$ group; R$^3$, R$^4$ and R$^5$ are independently an alkylene group or an arylene group; X is a —O—, —S— or =NR$^{10}$; R$^6$ and R$^7$ are independently hydrogen, an optionally substituted amino group or an optionally substituted alkyl group; R$^8$ and R$^9$ are independently an optionally substituted alkyl group (optionally with at least one substituent selected from the group consisting of an alcohol, amide, ether, ester or sulfonate group), an optionally substituted aryl group or a —SiR$^{11}$R$^{12}$R$^{13}$ group; R$^{10}$ is an alkyl, aryl or acyl group; and R$^{11}$, R$^{12}$ and R$^{13}$ are independently an optionally substituted alkoxy or alkyl group.

Aspects of the present invention are also realized with a (3,4-alkylenedioxythiophene) polymer derived from the above-disclosed thiophene compound.

Aspects of the present invention are also realized with a process for the polymerization of the above-disclosed thiophene.

Aspects of the present invention are realized with a solution or dispersion containing the above-disclosed (3,4-alkylenedioxythiophene) polymer.

Aspects of the present invention are also provided by the use of the above-disclosed solution or dispersion for coating an object.

Aspects of the present invention are also realized with a printable paste containing the above-disclosed (3,4-alkylenedioxythiophene) polymer.

Aspects of the present invention are also realized with an electroconductive layer containing the above-disclosed (3,4-alkylenedioxythiophene) polymer.

Aspects of the present invention are also realized with an antistatic layer containing the above-disclosed (3,4-alkylenedioxythiophene) polymer.

Further aspects of the present invention are disclosed in the dependent claims.

DETAILED DESCRIPTION OF THE INVENTION

Definitions

The term $C_{1-5}$-alkylene group represents methylene, 1,2-ethylene, 1,3-propylene, 1,4-butylene and 1,5-pentylene groups.

The term alkyl means all variants possible for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethylpropyl, 2,2-dimethylpropyl and 2-methyl-butyl etc.

The term (3,4-alkylenedioxythiophene) polymer encompasses homopolymers, copolymers and terpolymers including both (3,4-alkylenedioxythiophene) monomers and/or non-(3,4-alkylenedioxythiophene) monomers.

The term aqueous for the purposes of the present invention means containing at least 60% by volume of water, preferably at least 80% by volume of water, and optionally containing water-miscible organic solvents such as alcohols e.g. methanol, ethanol, 2-propanol, butanol, iso-amyl alcohol, octanol, cetyl alcohol etc.; glycols e.g. ethylene glycol; glycerine; N-methyl pyrrolidone; methoxypropanol; and ketones e.g. 2-propanone and 2-butanone etc.

The term conductive layer as used in disclosing the present invention includes both electroconductive coatings and antistatic layers.

The term electroconductive means having a surface resistance below $10^6$ Ω/square.

The term antistatic means having a surface resistance in the range from $10^6$ to $10^{11}$ Ω/square meaning it cannot be used as an electrode.

The term "conductivity enhancement" refers to a process in which the conductivity is enhanced e.g. by contact with one or more high boiling point liquids such as di- or polyhydroxy- and/or carboxy groups or amide or lactam group containing organic compound optionally followed by heating at elevated temperature, preferably between 100 and 250° C., during preferably 1 to 90 seconds, results in conductivity increase. Alternatively in the case of aprotic compounds with a dielectric constant $\geq 15$, e.g. N-methyl-pyrrolidinone, temperatures below 100° C. can be used. Such conductivity enhancement is observed with polythiophenes and can take place during the preparation of the outermost layer or subsequently. Particularly preferred liquids for such treatment are N-methyl-pyrrolidinone and diethylene glycol such as disclosed in EP-A 686 662 and EP-A 1 003 179.

PSS as used in the present disclosure represents poly(styrenesulfonic acid) or poly(styrenesulphonate).

PET as used in the present disclosure represents poly(ethylene terephthalate).

Thiophene Compound Represented by Formula (I)

Aspects of the present invention are realized with a thiophene compound represented by formula (I):

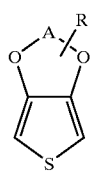

(I)

in which A represents a $C_{1-5}$-alkylene bridge; R represents a —$R^1$—(C=O)—$R^2$ group; —$R^1$— represents a —$R^3$— or —$R^4$—X—$R^5$— group; $R^2$ is hydrogen, a hydroxy group, a thiol group, —$NR^6R^7$, —$OR^8$ or a —$SR^9$ group; $R^3$, $R^4$ and $R^5$ are independently an alkylene group or an arylene group; X is a —O—, —S— or =$NR^{10}$; $R^6$ and $R^7$ are independently hydrogen, an optionally substituted amino group or an optionally substituted alkyl group; $R^8$ and $R^9$ are independently an optionally substituted alkyl group (optionally with at least one substituent selected from the group consisting of an alcohol, amide, ether, ester or sulfonate group), an optionally substituted aryl group or a —$SiR^{11}R^{12}R^{13}$ group; $R^{10}$ is an alkyl, aryl or acyl group; and $R^{11}$, $R^{12}$ and $R^{13}$ are independently an optionally substituted alkoxy or alkyl group.

According to a first embodiment of the thiophene compound according to the present invention, in the thiophene compound according to formula (I) $R^2$ is a hydroxy, an optionally substituted alkoxy group (optionally with at least one substituent selected from the group consisting of an alcohol, amide, ether, ester or sulfonate group) or an optionally substituted aryloxy group.

According to a second embodiment of the thiophene compound, according to the present invention, the thiophene compound is selected from the group consisting of: (2,3-dihydro-thieno[3,4-b][1,4]dioxin-2-yl-methoxy)-acetic acid, (2,3-dihydro-thieno[3,4-b][1,4]dioxin-2-ylmethoxy)-acetic acid methyl ester, (2,3-dihydro-thieno[3,4-b][1,4] dioxin-2-ylmethoxy)-acetic acid ethyl ester and (2,3-dihydro-thieno[3,4-b][1,4]dioxin-2-ylmethoxy)-acetic acid propyl ester.

Suitable thiophene compounds according to the present invention are:

| Thiophene compound nr. | Structural formula | |
|---|---|---|
| M1 | | (2,3-dihydro-thieno[3,4-b][1,4]dioxin-2-ylmethoxy)-acetic acid ethyl ester |
| M2 | | (2,3-dihydro-thieno[3,4-b][1,4]dioxin-2-yl-methoxy)-acetic acid |

| Thiophene compound nr. | Structural formula | |
|---|---|---|
| M3 | | (2,3-dihydro-thieno[3,4-b][1,4]dioxin-2-ylmethoxy)-acetic acid methyl ester |
| M4 | | (2,3-dihydro-thieno[3,4-b][1,4]dioxin-2-ylmethoxy)-acetic acid propyl ester |
| M5 | | (2,3-dihydro-thieno[3,4-b][1,4]dioxin-2-ylmethoxy)-acetic acid t-butyl ester |
| M6 | | (2,3-dihydro-thieno[3,4-b][1,4]dioxin-2-ylmethoxy)-acetic acid octadecyl ester |
| M7 | | (2,3-dihydro-thieno[3,4-b][1,4]dioxin-2-ylmethoxy)-acetic acid polyethylene oxide ester |

-continued
| Thiophene compound nr. | Structural formula | |
|---|---|---|
| M8 | 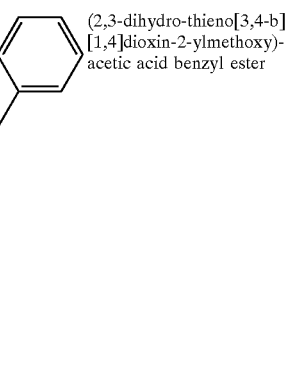 | (2,3-dihydro-thieno[3,4-b][1,4]dioxin-2-ylmethoxy)-acetic acid benzyl ester |
| M9 | 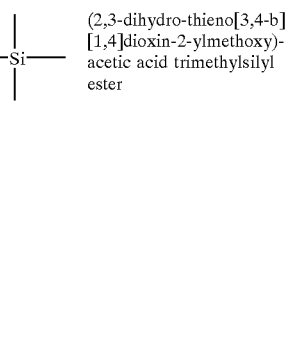 | (2,3-dihydro-thieno[3,4-b][1,4]dioxin-2-ylmethoxy)-acetic acid trimethylsilyl ester |
| M10 | 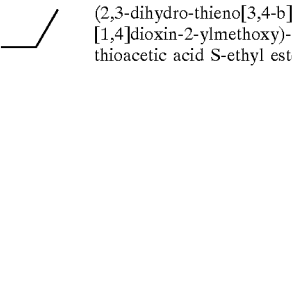 | (2,3-dihydro-thieno[3,4-b][1,4]dioxin-2-ylmethoxy)-thioacetic acid S-ethyl ester |
| M11 | 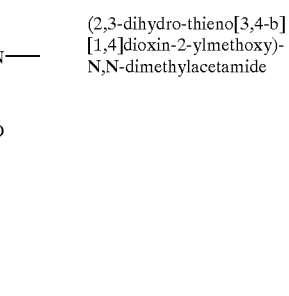 | (2,3-dihydro-thieno[3,4-b][1,4]dioxin-2-ylmethoxy)-N,N-dimethylacetamide |

-continued

| Thiophene compound nr. | Structural formula | |
|---|---|---|
| M12 | | (2,3-dihydro-thieno[3,4-b][1,4]dioxin-2-ylmethoxy)-acetic acid hydrazide |
| M13 | | (2,3-dihydro-thieno[3,4-b][1,4]dioxin-2-yl)-ethoxy]-acetic acid ethyl ester |
| M14 | | (2,3-dihydro-thieno[3,4-b][1,4]dioxin-2-yl)-propoxy]-acetic acid |
| M15 | | (2,3-dihydro-thieno[3,4-b][1,4]dioxin-2-yl)-ethoxy]-acetic acid |

Thiophene compounds according to formula (I), according to the present invention, can be prepared by known methods such the transetherification reaction disclosed in DE 3804522 and in HOUBEN-WEYL, volume VI/3, part 3, pages 171–173 (1971) using a thiophene derivative such as 3,4-dimethoxythiophene, or the double Williamson reaction as disclosed in 1994 in Electrochimica Acta in volume 39, pages 1345–1347 using a thiophene derivative such as the dimethyl ester of 3,4-dihydroxythiophene-2,5-dicarboxylic acid.

The monomers M3–M12 can be prepared from M2 applying well-known methods as described in the book Protective Groups in Organic Synthesis (Eds.: T. W. Green and P. G. M. Wuts), Wiley-New York, second edition (1991) and references therein. M13 and can be prepared in a similar way to M1 and M14 and M15 in a similar way to M2.

(3,4-alkylenedioxy-thiophene) polymer derived from a thiophene compound according to formula (I)

Aspects of the present invention are realized with a (3,4-alkylenedioxythiophene) polymer derived from a thiophene compound according to formula (I).

According to a first embodiment of the (3,4-alkylenedioxythiophene) polymer, according to the present invention, $R^1$ in formula (I) represents a —$CH_2OCH_2$— group.

According to a second embodiment of the (3,4-alkylenedioxythiophene) polymer, according to the present invention, the (3,4-alkylenedioxy-thiophene) polymer is selected from the group consisting of: poly[(2,3-dihydro-thieno[3,4-b][1,4]dioxin-2-yl-methoxy)-acetic acid], poly ([2,3-dihydro-thieno[3,4-b][1,4]dioxin-2-ylmethoxy)-acetic acid methyl ester], poly[(2,3-dihydro-thieno[3,4-b][1,4]dioxin-2-ylmethoxy)-acetic acid ethyl ester] and poly[(2,3-dihydro-thieno[3,4-b][1,4]dioxin-2-ylmethoxy)-acetic acid propyl ester].

Polymerization Process

Aspects of the present invention are also realized with a process for the polymerization of a thiophene according to formula (I).

According to a first embodiment of the polymerization process, according to the present invention, the process is a chemical or an electrochemical process.

Chemical Polymerization of Thiophene Compounds According to Formula (I)

Chemical polymerization, according to the present invention, can be carried out oxidatively or reductively. The oxidation agents used for the oxidative polymerisation of pyrrole, such as described for example in Journal of the American Chemical Society, volume 85, pages 454–458 (1963) and J. Polymer Science Part A Polymer Chemistry, volume 26, pages 1287–1294 (1988), can be utilized for the oxidative polymerization of thiophenes.

According to a second embodiment of the polymerization process, according to the present invention, the process is a chemical process in which the inexpensive and easily accessible oxidation agents such as iron(III) salts such as $FeCl_3$, the iron(III) salts of organic acids, e.g. $Fe(OTs)_3$, $H_2O_2$, $K_2Cr_2O_7$, alkali and ammonium persulphates, alkali perborates and potassium permanganate are used therein to initiate the p[olymerization.

Theoretically the oxidative polymerization of thiophenes requires 2.25 equivalents of oxidation agent per mole thiophene of formula (I) [(see e.g. J. Polymer Science Part A Polymer Chemistry, volume 26, pages 1287–1294 (1988)]. In practice an excess of 0.1 to 2 equivalents of oxidation agent is used per polymerizable unit. The use of persulphates and iron(III) salts has the great technical advantage that they do not act corrosively. Furthermore, in the presence of particular additives oxidative polymerization of the thiophene compounds according to formula (I) proceeds so slowly that the thiophenes and oxidation agent can be brought together as a solution or paste and applied to the substrate to be treated. After application of such solutions or pastes the oxidative polymerization can be accelerated by heating the coated substrate as disclosed in U.S. Pat. No. 6,001,281 and WO 00/14139 herein incorporated by reference.

Reductive polymerization can be carried out using Stille (organotin) routes or Suzuki (organoboron) routes as disclosed in 2001 in Tetrahedron Letters, volume 42, pages 155–157 and in 1998 in Macromolecules, volume 31, pages 2047–2056 respectively or with nickel complexes as disclosed in 1999 in Bull. Chem. Soc. Japan, volume 72, page 621 and in 1998 in Advanced Materials, volume 10, pages 93–116.

Electrochemical Polymerization of Thiophene Compounds According to Formula (I)

Thiophene compounds according to formula (I) can be polymerized electrochemically. Electrochemical oxidative polymerization of thiophene compounds according to formula (I) carried out at temperatures from −78° C. to the boiling point of the solvent employed, temperatures between −20° C. and 60° C. is preferred. The reaction time, depending upon the particular thiophene, is generally between a few seconds and several hours. Electrochemical olymerization of thiophene compounds was described in 1994 by Dietrich et al. in Journal Electroanalytical Chemistry, volume 369, pages 87–92.

Inert liquids suitable for use during electrochemical oxidation of thiophene compounds according to formula (I) are: water, alcohols such as methanol and ethanol, ketones such as acetophenone, halogenated hydrocarbons such as methylene chloride, chloroform, tetrachloromethane and fluorohydrocarbons, esters such as ethyl acetate and butyl acetate, aromatic hydrocarbons such as benzene, toluene and xylene, aliphatic hydrocarbons such as pentane, hexane, heptane and cyclohexane, nitriles such as acetonitrile and benzonitrile, sulfoxides such as dimethylsulfoxide, sulfones such as dimethylsulfone, phenylmethylsulfone and sulfolan, liquid aliphatic amides such as methyl acetamide, dimethyl acetamide, dimethyl formamide, pyrrolidone, N-methyl-pyrrolidone, caprolactam, N-methyl-caprolactam, aliphatic and mixed aliphatic and aromatic ethers such as diethylether and anisole, liquid ureas such as tetramethylurea or N,N-dimethyl-imidazolidinone.

Electrolyte additives for use in the electrochemical polymerization of thiophene compounds according to formula (I) are preferably free acids or the usual conducting salts, which exhibit a certain solubility in the solvent used. Particularly suitable electrolytes are alkali, alkaline earth or optionally alkylated ammonium, phosphonium, sulfonium or oxonium cations in combination with perchlorate, tosylate, tetrafluoroborate or hexafluorophosphonate anions.

The electrolyte additives are used in such quantities, that a current of at least 0.1 mA flows during electrochemical oxidation.

Electrochemical polymerization can be carried out continuously or discontinuously. Known electrode materials are ITO-covered glass, precious metal or steel mesh, carbon-filled polymers, evaporated metal-coated insulator layers and carbon felt.

Current densities during electrochemical oxidation may vary within wide limits. According to an eighth embodiment of the present invention the current densities is 0.0001 to 100 mA/cm$^2$. According to a third embodiment of the process, according to the present invention, the current density is 0.01 to 40 mA/cm$^2$. At these current densities voltages of ca. 0.1 to 50 V are set up.

Thiophene compounds according to formula (I) may also be electrochemically copolymerized with other polymerizable heterocyclic compounds such as pyrrole.

Solution or dispersion containing a poly(3,4-alkylenedioxythiophene) derived from a thiophene according to formula (I)

According to a first embodiment of the solution or dispersion according to the present invention, the solution or dispersion further contains a polyanion.

According to a second embodiment of the solution or dispersion according to the present invention, the solution or dispersion further contains poly(styrenesulphonic acid).

According to a third embodiment of the solution or dispersion according to the present invention, the medium is an aqueous medium.

Polyanion

The polyanion compounds for use in the solution or dispersion according to the present invention are disclosed in EP-A 440 957 and include polymeric carboxylic acids, e.g. polyacrylic acids, polymethacrylic acids, or polymaleic acids and polysulphonic acids, e.g. poly(styrenesulphonic acid). These polycarboxylic acids and polysulphonic acids can also be copolymers of vinylcarboxylic acids and vinylsulphonic acids with other polymerizable monomers, e.g. acrylic acid esters, methacrylic acid esters and styrene.

Industrial Application

Chemically or electrochemically prepared polymers derived from thiophene compounds according to formula (I) exhibit high electrical conductivity together with low absorption of visible light and high absorption to infrared radiation. Therefore layers thereof are highly electrically conducting, highly transparent to visible light and heat shielding. Such polythiophenes can be applied to a wide variety of rigid and flexible substrates, e.g. ceramics, glass and plastics, and are particularly suitable for flexible substrates such as plastic sheeting and the substrates can be substantially bent and deformed without the polythiophene layer losing its electrical conductivity.

Such polythiophenes can therefore be utilized, for example, in photovoltaic devices, batteries, capacitors and organic and inorganic electroluminescent devices, in electromagnetic shielding layers, in heat shielding layers, in antistatic coatings for a wide variety of products including photographic film, thermographic recording materials and photothermographic recording materials, in smart windows, in electrochromic devices, in sensors for organic and bio-organic materials, in field effect transistors, in printing plates, in conductive resin adhesives and in free-standing electrically conductive films [see also chapter 10 of the Handbook of Oligo- and Polythiophenes, Edited by D. Fichou, Wiley-VCH, Weinheim (1999)].

The invention is illustrated hereinafter by way of comparative and invention examples. The percentages and ratios given in these examples are by weight unless otherwise indicated.

Synthesis of Monomers

Synthesis of 2-acetoxymethyl-2,3-dihydro-thieno[3,4-b][1,4]dioxine-5,7-dicarboxylic acid dimethyl ester

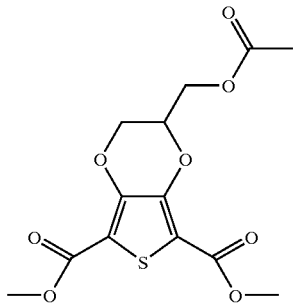

A 70/30 molar mixture of 2-acetoxymethyl-2,3-dihydro-thieno[3,4-b][1,4]dioxine-5,7-dicarboxylic acid dimethyl ester and 3-acetoxy-3,4-dihydro-2H-thieno[3,4-b][1,4]dioxepine-6,8-dicarboxylic acid dimethyl ester was obtained by performing the reaction between 3,4-dihydroxythiophene-2,5-dicarboxylic acid dimethyl ester and epibromohydrin as described in U.S. Pat. No. 5,111,327. This mixture was subsequently separated by an acetylation/selective crystallization procedure: the 70/30 molar mixture of 2-acetoxymethyl-2,3-dihydro-thieno[3,4-b][1,4]dioxine-5,7-dicarboxylic acid dimethyl ester and 3-acetoxy-3,4-dihydro-2H-thieno[3,4-b][1,4]dioxepine-6,8-dicarboxylic acid dimethyl ester (143 g, 0.496 mol) was dissolved in methylene chloride (1.5 L). Triethylamine (80 mL) was subsequently added after which acetyl chloride (43 mL) was added dropwise, constantly keeping the reaction around 25° C. by slight cooling. After addition the mixture was stirred for another hour at 25° C.

Subsequently, the reaction mixture was washed several times with 1M hydrochloric acid, a 1M aqueous solution of sodium hydrogen carbonate and a saturated aqueous solution of sodium chloride, respectively. The solvent was removed and the resulting solid was recrystallized from ethanol. After filtration and washing of the residue, pure 2-acetoxymethyl-2,3-dihydro-thieno[3,4-b][1,4]dioxine-5,7-dicarboxylic acid dimethyl ester was obtained as demonstrated by NMR and mass spectroscopy.

Synthesis of 3-acetoxy-3,4-dihydro-2H-thieno[3,4-b][1,4]dioxepine-6,8-dicarboxylic acid dimethyl ester

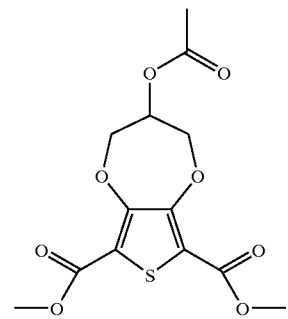

Its seven-membered ring isomer, 3-acetoxy-3,4-dihydro-2H-thieno[3,4-b][1,4]dioxepine-6,8-dicarboxylic acid dimethyl ester, could be isolated by concentrating the filtrate of the above-mentioned recrystallization process. The remaining residue, being a mixture of 2-acetoxymethyl-2,3-dihydro-thieno[3,4-b][1,4]dioxine-5,7-dicarboxylic acid dimethyl ester and 3-acetoxy-3,4-dihydro-2H-thieno[3,4-b][1,4]dioxepine-6,8-dicarboxylic acid dimethyl ester (molar ratio ca. 1:2) was subsequently separated into the individual compounds by column chromatography using $SiO_2$ (eluant: $CH_2Cl_2$/ethylacetate=90/10). This finally resulted in pure 3-acetoxy-3,4-dihydro-2H-thieno[3,4-b][1,4]dioxepine-6,8-dicarboxylic acid dimethyl ester as well as some additional pure 2-acetoxymethyl-2,3-dihydro-thieno[3,4-b][1,4]dioxine-5,7-dicarboxylic acid dimethyl ester.

Synthesis of 2-hydroxymethyl-2,3-dihydro-thieno[3,4-b][1,4]dioxine-5,7-dicarboxylic acid

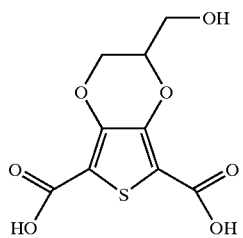

2-Acetoxymethyl-2,3-dihydro-thieno[3,4-b][1,4]dioxine-5,7-dicarboxylic acid dimethyl ester (60 g, 0.18 mol) was dissolved in ethanol (680 mL). KOH (36 g) was added to this solution after which water (500 mL) was added upon continuous cooling. After addition of the water the reaction mixture was stirred for another 30 minutes after which the solvents were removed by distillation. To the remaining part of the reaction mixture, we dropwise added a mixture of ice (50 g) and concentrated hydrochloric acid (25 mL), and stirred. The mixture was then filtrated and the residue was washed with water. Subsequent drying resulted in quantitative formation of pure 2-hydroxymethyl-2,3-dihydro-thieno[3,4-b][1,4]dioxine-5,7-dicarboxylic acid as demonstrated by NMR and mass spectroscopy.

Synthesis of (2,3-dihydro-thieno[3,4-b][1,4]dioxin-2-yl)-methanol

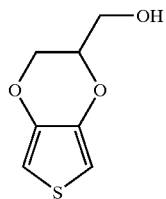

2-Hydroxymethyl-2,3-dihydro-thieno[3,4-b][1,4]dioxine-5,7-dicarboxylic acid (48 g, 0.184 mol) was dissolved in N,N-dimethylacetamide (500 mL), and $Cu_2Cr_2O_7$ (8.6 g) and quinoline (15 drops) were added. This mixture was subsequently stirred for 2 hours at 150° C., after which it was cooled to 25° C. It was then poured into ethyl acetate, the catalyst removed by filtration and the filtrate washed with acidic water and a saturated aqueous solution of sodium chloride. The solvent was then removed after which pure (2,3-dihydro-thieno[3,4-b][1,4]dioxin-2-yl)-methanol was isolated by vacuum distillation (115–120° C.; 0.05 mm Hg).

Synthesis of (2,3-dihydro-thieno[3,4-b][1,4]dioxin-2-ylmethoxy)-acetic acid ethyl ester (M1)

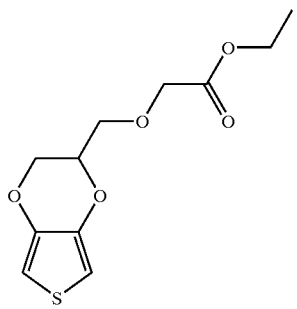

(2,3-Dihydro-thieno[3,4-b][1,4]dioxin-2-yl)-methanol (6.9 g, 40 mmol) was dissolved into tetrahydrofuran (100 mL), blanketed by nitrogen. Sodium hydride (1.9 g) was added in portions after which the reaction mixture was stirred for another 30 min. Then ethyl bromoacetate (5.3 mL) was added dropwise and stirring was continued for another hour at 25° C. The reaction mixture was then poured into ethyl acetate, washed with 1M hydrochloric acid, washed with a 1M aqueous solution of sodium hydrogen carbonate and concentrated. This resulted in quantitative formation of pure (2,3-dihydro-thieno[3,4-b][1,4]dioxin-2-ylmethoxy)-acetic acid ethyl ester as demonstrated by NMR and mass spectroscopy.

Synthesis of (2,3-dihydro-thieno[3,4-b][1,4]dioxin-2-yl-methoxy)-acetic acid (M2)

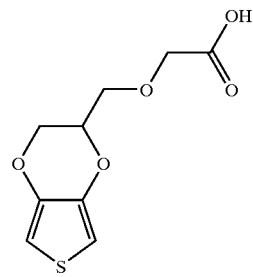

(2,3-Dihydro-thieno[3,4-b][1,4]dioxin-2-ylmethoxy)-acetic acid ethyl ester (10.2 g, 40 mmol) was dissolved into ethanol (100 mL) and water (50 mL), blanketed by nitrogen. Potassium hydroxide (2.9 g) was added and the mixture was heated at 35° C. for 30 min. The solvents were then removed by distillation, ethyl acetate (50 mL), ice-water (50 mL) and concentrated hydrochloric acid (5 mL) were added and the mixture was vigorously stirred. Subsequently, the organic phase was separated, washed with a saturated aqueous solution of sodium chloride, dried with anhydrous magnesium sulphate and concentrated. Finally the raw product was recrystallized from ethyl acetate/hexanes (1/1) resulting in pure (2,3-dihydro-thieno[3,4-b][1,4]dioxin-2-ylmethoxy)-acetic acid as demonstrated by NMR and mass spectroscopy.

Preparation of 3,4-alkylenedioxythiophene-homopolymers

COMPARATIVE EXAMPLE 1

At 25° C., 562.5 g of a 5.6% by weight aqueous solution of poly(styrenesulphonic acid) [PSS] (Mw=290,000), 2437.5 g of deionized water and 12.78 g (90 mmol) EDOT were mixed in a 4 L reaction vessel equipped with a stirrer.

0.225 g $Fe_2(SO_4)_3 \cdot 9H_2O$ and 25.7 g $Na_2S_2O_8$ were then added to initiate the polymerization reaction. The reaction mixture was stirred at 25° C. for 7 h, after which a further 4.3 g of $Na_2S_2O_8$ was added. After an additional reaction time of 16 h the reaction mixture was treated 2 times with ion exchanger (300 ml Lewatit™ S100 MB+500 ml Lewatit™ M600 MB from BAYER). The resulting mixture was additionally thermally treated at 95° C. for 2 h and the resulting viscous mixture treated with high shear (microfluidizer at 600 Bar). This procedure yielded 1800 g of a 1.09 wt % blue dispersion of PEDOT1.

COMPARATIVE EXAMPLE 2

At 25° C., 438.23 g of a 5.99% by weight aqueous solution of poly(styrene sulphonic acid)[PSS] (Mw=290,000) and 2061.77 g deionized water were mixed in a 4 L reaction vessel equipped with a stirrer and a nitrogen inlet. After bubbling nitrogen through this mixture for 30 minutes, 12.78 g (90 mmol) of EDOT were added to this solution. 0.225 g $Fe_2(SO_4)_3 \cdot 9H_2O$ and 25.7 g $Na_2S_2O_8$ were then added to initiate the polymerization reaction. The reaction mixture was stirred at 25° C. for 7 h, after which a further 4.3 g of $Na_2S_2O_8$ was added. After an additional reaction time of 16 h the reaction mixture was treated 2 times with ion exchanger (300 ml Lewatit™ S100 MB+500 ml Lewatit™ M600 MB). The resulting mixture was additionally thermally treated at 95° C. for 2 h and the resulting viscous mixture treated with high shear (microfluidizer at 600 Bar). This procedure yielded 1950 g of a 1.02 wt % blue dispersion of PEDOT2.

COMPARATIVE EXAMPLE 3

At 25° C., 438.23 g of a 5.99% by weight aqueous solution of poly(styrene sulphonic acid)[PSS] (Mw=290,000) and 2061.77 g deionized water were mixed in a 4 L reaction vessel equipped with a stirrer and a nitrogen inlet. After bubbling nitrogen purging through this mixture for 30 minutes, 12.78 g (90 mmol) of EDOT was added. 0.225 g $Fe_2(SO_4)_3 \cdot 9H_2O$ and 25.7 g $Na_2S_2O_8$ were then added to initiate the polymerization reaction. The reaction mixture was stirred at 25° C. for 7 h, after which a further 4.3 g of $Na_2S_2O_8$ was added. After an additional reaction time of 16 h the reaction mixture was treated 2 times with ion exchanger (300 ml Lewatit™ S100 MB+500 ml Lewatit™ M600 MB). The resulting mixture was additionally thermally treated at 95° C. for 2 h and the resulting viscous mixture was treated with high shear (microfluidizer at 600 Bar). This procedure yielded 1840 g of a 1.03 wt % blue dispersion of PEDOT3.

Preparing Electroconductive Layers with Dispersions Based on the Dispersions of Comparative Examples 1 to 3

Coating dispersions were produced by adding 3-glycidoxypropyl-trimethoxysilane, ZONYL® FSO100, a copolymer latex of vinylidene chloride, methacrylate and itaconic acid (88/10/2) and N-methyl pyrrolidinone to the dispersions of COMPARATIVE EXAMPLES 1 to 3 so as to produce layers, upon doctor blade-coating onto a subbed 175 μm poly(ethylene terephthalate) support and drying at 45° C. for 3.5 minutes, with the following composition:

| | |
|---|---|
| PEDOT | 28.9 mg/m$^2$ |
| [PEDOT)/PSS | 100 mg/m$^2$] |
| ZONYL ® FSO100 | 8 mg/m$^2$ |
| 3-glycidoxypropyl-trimethoxysilane | 100 mg/m$^2$ |
| Copolymer latex of vinylidene chloride, methacrylate and itaconic acid (88/10/2) | 100 mg/m$^2$ |
| N-methyl pyrrolidinone | 2 mL/m$^2$ |

Characterization of Electroconductive Layers Prepared with Dispersions Based on Dispersions of Comparative Examples 1 to 3

The optical density of the layers was determined by measuring a stack of 10 strips with a Macbeth® TD904 densitometer using a visible filter and then obtaining therefrom the optical density of a single strip. The values given in Table 1 include the optical density of the PET-support.

The surface resistance of the layers was measured in a room conditioned to a temperature of 25° C. and 30% relative humidity by contacting the printed layer with parallel copper electrodes each 35 mm long and 35 mm apart capable of forming line contacts, the electrodes being separated by a Teflon® insulator. This enabled a direct measurement of the surface resistance to be realized. The results are also summarized in Table 1.

The layers were then exposed to artificial sunlight (provided by a xenon lamp) through a glass filter in an Atlas Material Testing Technology BV, SUNTEST™ CPS apparatus according to DIN 54 004. The factor given in Table 1 is the ratio of surface resistance after x hours Suntest™ exposure to the surface resistance before the Suntest exposure.

TABLE 1

| | | PEDOT/PSS | | Initial surface | | Ratio of surface resistance |
|---|---|---|---|---|---|---|
| Comparative Example nr | Condition of reaction medium prior to initiator addition | | Concentration [wt %] | resistance [Ohm/square] | O.D. | after 48 h Suntest ™ exposure to initial surface resistance |
| 1 | no oxygen exclusion | PEDOT1 | 1.09 | 2900 | 0.067 | 83 |
| 2 | O$_2$ purged by N$_2$ bubble through | PEDOT2 | 1.02 | 1200 | 0.066 | 13 |
| 3 | O$_2$ purged by N$_2$ bubble through | PEDOT3 | 1.03 | 1200 | 0.065 | 12 |

The results in Table 1 show that the initial surface resistance and the stability of the PEDOT/PSS-layers is strongly dependent upon the conditions under which the polymerization is initiated, driving off oxygen by bubbling through with nitrogen resulting in lower surface resistance and higher stability to 48 h Suntest™ exposure as shown by lower ratios of surface resistance after Suntest™ exposure to the initial surface resistance.

Electrochemical Polymerization of EDOT and M2

Electropolymerization was performed at 25° C. using a standard three electrode cell. The working electrode was platinum, gold or indium-tin-oxide. The counter electrodes was platinum; the reference electrode was silver/0.1 M silver perchlorate in acetonitrile (0.34 V vs SCE).

Acetonitrile solutions $10^{-3}$ to $10^{-2}$ M in the monomer of COMPARATIVE EXAMPLE 4 and INVENTION EXAMPLE 1 (EDOT and M2 respectively) and 0.1 M in $NaClO_4$ were polymerized by applying a potential of 0.7–0.9 V in the cell. A current density of 5 mA $cm^{-2}$ was used in the electropolymerization.

In-situ Electrical Conductivity Measurements

Electrical conductivity measurements were carried out in the absence of monomer in the same three electrode cell in which the electropolymerization was carried out. The electrode for conductivity measurements was a two-band platinum electrode (0.3 cm×0.01 cm for each band) with an interband spacing of 20 μm. The platinum electrode was coated with polymer by the passage of 80 mC, which assured the attainment of limiting resistance conditions. Electrical conductivities were measured by applying a small amplitude (typically 10 mV) DC voltage between the bands and recording the current thereby obtained. Poly(3-methylthiophene) (60 S/cm) was used as an electrical conductivity standard. The results are shown in Table 2.

TABLE 2

Surface resistance of layers of electropolymerized homopolymers

| Polymer nr. | monomer nr. | Resistivity [ohm-cm] | Conductivity [S/cm] |
|---|---|---|---|
| | Comparative Example nr | | |
| 4 | PEDOT 4 | EDOT  $1.67 \times 10^{-3}$ | 599 |
| | Invention Example nr | | |
| 1 | P1 | M2  $2.5 \times 10^{-3}$ | 400 |

The results in Table 2 show that electropolymerized homopolymers of EDOT (PEDOT4) and M2 (P1) exhibited comparable resistivities to one another.

Preparation of 3,4-alkylenedioxythiophene-copolymers

INVENTION EXAMPLES 2 AND 3

The dispersions of the 3,4-alkylenedioxythiophene copolymers of INVENTION EXAMPLES 2 and 3 were prepared by mixing 87 g of a 5.99% by weight aqueous solution of poly(styrenesulphonic acid) [PSS] (Mw=290,000) with 413 g of deionized water at 25° C. in a 1 L reaction vessel equipped with a stirrer and a nitrogen inlet. After bubbling nitrogen through this mixture for 30 minutes, EDOT (for quantity see Table 3) and M2 (for quantity see Table 3) were added to this solution. Nitrogen was then again bubbled through the reaction mixture for 30 minutes. 0.0375 g $Fe_2(SO_4)_3$ and 4.28 g $Na_2S_2O_8$ were then added to initiate the copolymerization reaction. The reaction mixture was stirred at 25° C. for 7 h, after which a further 0.7 g of $Na_2S_2O_8$ was added. After an additional reaction time of 16 h the reaction mixture was treated twice with ion exchanger (50 ml Lewatit™ S100 MB+80 ml Lewatit™ M600 MB from BAYER). The resulting mixture was additionally thermally treated at 95° C. for 2 h and the resulting viscous mixture diluted and treated with high shear (microfluidizer at 600 Bar). This procedure yielded a dispersion of the copolymer (for type, quantity produced and concentration of copolymer in the dispersion see Table 3).

TABLE 3

| INVENTION EXAMPLE NUMBER | 2 | 3 |
|---|---|---|
| EDOT wt [g] | 1.92 | 1.7 |
| EDOT, molar quantity [mmoles] | 13.5 | 11.96 |
| M2, wt [g] | 0.345 | 0.69 |
| M2, molar quantity of [mmoles] | 1.49 | 3.00 |
| Copolymer dispersion | CP1 | CP2 |
| wt of (co)polymer dispersion prepared [g] | 450 | 455 |
| (co)polymer concentration in dispersion [wt %] | 0.76 | 1.14 |

Characterization of the PEDOT of Comparative Examples 2 and 3 and the Copolymers of Invention Examples 2 and 3

The molecular weights of the copolymers and the PEDOT of COMPARATIVE EXAMPLES 2 and 3 were determined by aqueous gel permeation chromatography relative to sodium poly(styrene sulphonate) with UV-vis absorption detection at 785 nm.

The molecular weights of the copolymers and PEDOT together with their concentrations in the dispersions produced with reaction media purged of oxygen by bubbling of nitrogen prior to the addition of initiator and the theoretical concentration in mol % in the comonomer are summarized in Table 4.

TABLE 4

| (Co)polymer nr. | Comonomer Nr. | Comonomer mol % | Conc of Copolymer/PSS [wt %] | Molecular weight [785 nm] |
|---|---|---|---|---|
| PEDOT 2 | — | 0 | 1.02 | 490,000 |
| PEDOT 3 | — | 0 | 1.03 | 390,000 |
| CP1 | M2 | 10 | 0.76 | 560,000 |
| CP2 | M2 | 20 | 1.14 | 540,000 |

Preparation of Layers Produced with Dispersions Containing the Copolymers of Invention Examples 2 and 3

Coating dispersions were prepared with the dispersions of INVENTION EXAMPLES 2 and 3 as described above for the dispersion of COMPARATIVE EXAMPLES 1 to 3 so as to produce layers, upon doctor blade-coating onto a subbed 175 μm poly(ethylene terephthalate) support and drying at 45° C. for 3.5 minutes, with the following composition:

| | |
|---|---|
| Copolymer of ADOT and comonomer (or PEDOT) | 28.9 mg/m² |
| [copolymer of ADOT and comonomer (or PEDOT)/PSS | 100 mg/m²] |
| ZONYL ® FSO100 | 8 mg/m² |
| 3-glycidoxypropyl-trimethoxysilane | 100 mg/m² |
| Copolymer latex of vinylidene chloride, methacrylate and itaconic acid (88/10/2) | 100 mg/m² |
| N-methyl pyrrolidinone | 2 mL/m² |

Characterization of Layers Containing the Copolymers of Comparative Examples 2 and 3 and Invention Examples 2 and 3

The surface resistance, optical density and light stability of the layers containing the copolymers of INVENTION EXAMPLES 2 and 3 were determined as described above for the layers containing the homopolymers of COMPARATIVE EXAMPLES 1 to 3. The results are summarized in Table 5.

TABLE 5

Surface resistance and optical density of layers of PEDOT/PSSA copolymers

| | | Layer containing (co)polymer | | | | |
|---|---|---|---|---|---|---|
| | | Comonomer | | Surface resistance | Ratio of surface resistance after 48 h Suntest ™ exposure to initial surface resistance | O.D. |
| Example Nr | (Co)polymer nr. | nr. | mol % | [ohm/square] | | |
| COMP 2 | PEDOT 2 | — | 0 | 1200 | 13 | 0.066 |
| COMP 3 | PEDOT 3 | — | 0 | 1200 | 12 | 0.065 |
| INV 2 | CP1 | M2 | 10 | 2200 | 74 | 0.060 |
| INV 3 | CP2 | M2 | 20 | 2500 | 72 | 0.063 |

The copolymers of CP1 and CP2 exhibited comparable properties with those of the PEDOT of COMPARATIVE EXAMPLES 2 and 3 polymerized under comparable conditions i.e. in reaction media purged of oxygen through nitrogen bubbling prior to the addition of initiator.

The present invention may include any feature or combination of features disclosed herein either implicitly or explicitly or any generalisation thereof irrespective of whether it relates to the presently claimed invention. In view of the foregoing description it will be evident to a person skilled in the art that various modifications may be made within the scope of the invention.

We claim:

1. A thiophene compound represented by formula (I):

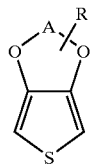

(I)

in which A represents a $C_{1-5}$-alkylene bridge; R represents a —$R^1$—(C=O)—$R^2$ group; —$R^1$— represents a —$R^3$— or —$R^4$—X—$R^5$— group; $R^2$ is hydrogen, a hydroxy group, a thiol group, —$NR^6R^7$, —$OR^8$ or a —$SR^9$ group; $R^3$, $R^4$ and $R^5$ are independently an alkylene group or an arylene group; X is a —O—, —S— or =$NR^{10}$; $R^6$ and $R^7$ are independently hydrogen, an optionally substituted amino group or an optionally substituted alkyl group; $R^8$ and $R^9$ are independently an optionally substituted alkyl group (optionally with at least one substituent selected from the group consisting of an alcohol, amide, ether, ester or sulfonate group), an optionally substituted aryl group or a —$SiR^{11}R^{12}R^{13}$ group; $R^{10}$ is an alkyl, aryl or acyl group; and $R^{11}$, $R^{12}$ and $R^{13}$ are independently an optionally substituted alkoxy or alkyl group.

2. Thiophene compound according to claim 1, wherein —$R^1$— represents a —$CH_2OCH_2$— group.

3. Thiophene compound according to claim 1, wherein said thiophene compound is selected from the group consisting of: (2,3-dihydro-thieno[3,4-b][1,4]dioxin-2-ylmethoxy)-acetic acid, (2,3-dihydro-thieno[3,4-b][1,4]dioxin-2-ylmethoxy)-acetic acid methyl ester, (2,3-dihydro-thieno[3,4-b][1,4]dioxin-2-ylmethoxy)-acetic acid ethyl ester and (2,3-dihydro-thieno[3,4-b][1,4]dioxin-2-ylmethoxy)-acetic acid propyl ester.

4. A (3,4-alkylenedioxy-thiophene) polymer derived from a thiophene compound represented by formula (I):

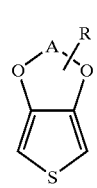

(I)

in which A represents a $C_{1-5}$-alkylene bridge; R represents a —$R^1$—(C=O)—$R^2$ group; —$R^1$— represents a —$R^3$— or —$R^4$—X—$R^5$— group; $R^2$ is hydrogen, a hydroxy group, a thiol group, —$NR^6R^7$, —$OR^8$ or a —$SR^9$ group; $R^3$, $R^4$ and $R^5$ are independently an alkylene group or an arylene group; X is a —O—, —S— or =$NR^{10}$; $R^6$ and $R^7$ are independently hydrogen, an optionally substituted amino group or an optionally substituted alkyl group; $R^8$ and $R^9$ are independently an optionally substituted alkyl group (optionally with at least one substituent selected from the group consisting of an alcohol, amide, ether, ester or sulfonate group), an optionally substituted aryl group or a —$SiR^{11}R^{12}R^{13}$ group; $R^{10}$ is an alkyl, aryl or acyl group; and $R^{11}$, $R^{12}$ and $R^{13}$ are independently an optionally substituted alkoxy or alkyl group.

5. (3,4-alkylenedioxy-thiophene) polymer according to claim 4, wherein said (3,4-alkylenedioxy-thiophene) polymer is selected from the group consisting of: poly[(2,3-dihydro-thieno[3,4-b][1,4]dioxin-2-yl-methoxy)-acetic acid], poly[(2,3-dihydro-thieno[3,4-b][1,4]dioxin-2-ylmethoxy)-acetic acid methyl ester], poly[(2,3-dihydro-thieno[3,4-b][1,4]dioxin-2-ylmethoxy)-acetic acid ethyl ester] and poly[(2,3-dihydro-thieno[3,4-b][1,4]dioxin-2-ylmethoxy)-acetic acid propyl ester].

6. A process for the polymerization of a thiophene compound represented by formula (I):

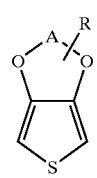

(I)

in which A represents a $C_{1-5}$-alkylene bridge; R represents a —$R^1$—(C=O)—$R^2$ group; —$R^1$— represents a —R³— or —R⁴—X—R⁵— group; R² is hydrogen, a hydroxy group, a thiol group, —NR⁶R⁷, —OR⁸ or a —SR⁹ group; R³, R⁴ and R⁵ are independently an alkylene group or an arylene group; X is a —O—, —S— or =NR¹⁰; R⁶ and R⁷ are independently hydrogen, an optionally substituted amino group or an optionally substituted alkyl group; R⁸ and R⁹ are independently an optionally substituted alkyl group (optionally with at least one substituent selected from the group consisting of an alcohol, amide, ether, ester or sulfonate group), an optionally substituted aryl group or a —SiR¹¹R¹²R¹³ group; R¹⁰ is an alkyl, aryl or acyl group; and R¹¹, R¹² and R¹³ are independently an optionally substituted alkoxy or alkyl group.

7. Process according to claim 6, wherein said process is a chemical or an electrochemical process.

8. A solution or dispersion containing a (3,4-alkylenedioxythiophene) polymer derived from a thiophene compound represented by formula (I):

(I)

in which A represents a $C_{1-5}$-alkylene bridge; R represents a —R¹—(C=O)—R² group; —R¹— represents a —R³— or —R⁴—X—R⁵— group; R² is hydrogen, a hydroxy group, a thiol group, —NR⁶R⁷, —OR⁸ or a —SR⁹ group; R³, R⁴ and R⁵ are independently an alkylene group or an arylene group; X is a —O—, —S— or =NR¹⁰; R⁶ and R⁷ are independently hydrogen, an optionally substituted amino group or an optionally substituted alkyl group; R⁸ and R⁹ are independently an optionally substituted alkyl group (optionally with at least one substituent selected from the group consisting of an alcohol, amide, ether, ester or sulfonate group), an optionally substituted aryl group or a —SiR¹¹R¹²R¹³ group; R¹⁰ is an alkyl, aryl or acyl group; and R¹¹, R¹² and R¹³ are independently an optionally substituted alkoxy or alkyl group.

9. Solution or dispersion according to claim 8 further containing a polyanion.

10. Solution or dispersion according to claim 9, wherein said polyanion is poly(styrenesulphonic acid).

11. Solution or dispersion according to claim 8, wherein the medium is an aqueous medium.

12. A process using a solution or dispersion containing a (3,4-alkylenedioxythiophene) polymer derived from a thiophene compound represented by formula (I):

(I)

in which A represents a $C_{1-5}$-alkylene bridge; R represents a —R¹—(C=O)—R² group; —R¹— represents a —R³— or —R⁴—X—R⁵— group; R² is hydrogen, a hydroxy group, a thiol group, —NR⁶R⁷, —OR⁸ or a —SR⁹ group; R³, R⁴ and R⁵ are independently an alkylene group or an arylene group; X is a —O—, —S— or =NR¹⁰; R⁶ and R⁷ are independently hydrogen, an optionally substituted amino group or an optionally substituted alkyl group; R⁸ and R⁹ are independently an optionally substituted alkyl group (optionally with at least one substituent selected from the group consisting of an alcohol, amide, ether, ester or sulfonate group), an optionally substituted aryl group or a —SiR¹¹R¹²R¹³ group; R¹⁰ is an alkyl, aryl or acyl group; and R¹¹, R¹² and R¹³ are independently an optionally substituted alkoxy or alkyl group for coating an object.

13. A printable paste containing a (3,4-alkylenedioxythiophene) polymer derived from a thiophene compound represented by formula (I):

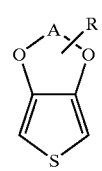

(I)

in which A represents a $C_{1-5}$-alkylene bridge; R represents a —R¹—(C=O)—R² group; —R¹— represents a —R³— or —R⁴—X—R⁵— group; R² is hydrogen, a hydroxy group, a thiol group, —NR⁶R⁷, —OR⁸ or a —SR⁹ group; R³, R⁴ and R⁵ are independently an alkylene group or an arylene group; X is a —O—, —S— or =NR¹⁰; R⁶ and R⁷ are independently hydrogen, an optionally substituted amino group or an optionally substituted alkyl group; R⁸ and R⁹ are independently an optionally substituted alkyl group (optionally with at least one substituent selected from the group consisting of an alcohol, amide, ether, ester or sulfonate group), an optionally substituted aryl group or a —SiR¹¹R¹²R¹³ group; R¹⁰ is an alkyl, aryl or acyl group; and R¹¹, R¹² and R¹³ are independently an optionally substituted alkoxy or alkyl group.

14. An electroconductive layer containing a (3,4-alkylenedioxythiophene) polymer derived from a thiophene compound represented by formula (I):

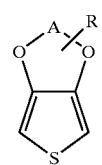

(I)

in which A represents a $C_{1-5}$-alkylene bridge; R represents a —R¹—(C=O)—R² group; —R¹— represents a —R³— or —R⁴—X—R⁵— group; R² is hydrogen, a hydroxy group, a thiol group, —NR⁶R⁷, —OR⁸ or a —SR⁹ group; R³, R⁴ and R⁵ are independently an alkylene group or an arylene group; X is a —O—, —S— or =NR¹⁰; R⁶ and R⁷ are independently hydrogen, an optionally substituted amino group or an optionally substituted alkyl group; R⁸ and R⁹ are independently an optionally substituted alkyl group (optionally with at least one substituent selected from the group consisting of an alcohol, amide, ether, ester or sulfonate group), an optionally substituted aryl group or a —SiR¹¹R¹²R¹³ group; R¹⁰ is an alkyl, aryl or acyl group; and $R^{11}$, $R^{12}$ and $R^{13}$ are independently an optionally substituted alkoxy or alkyl group.

15. An antistatic layer containing a (3,4-alkylenedioxythiophene) polymer derived from a thiophene compound represented by formula (I):

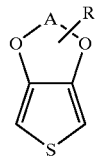

(I)

in which A represents a $C_{1-5}$-alkylene bridge; R represents a —$R^1$—(C=O)—$R^2$ group; —$R^1$— represents a —$R^3$— or —$R^4$—X—$R^5$— group; $R^2$ is hydrogen, a hydroxy group, a thiol group, —$NR^6R^7$, —$OR^8$ or a —$SR^9$ group; $R^3$, $R^4$ and $R^5$ are independently an alkylene group or an arylene group; X is a —O—, —S— or =$NR^{10}$; $R^6$ and $R^7$ are independently hydrogen, an optionally substituted amino group or an optionally substituted alkyl group; $R^8$ and $R^9$ are independently an optionally substituted alkyl group (optionally with at least one substituent selected from the group consisting of an alcohol, amide, ether, ester or sulfonate group), an optionally substituted aryl group or a —$SiR^{11}R^{12}R^{13}$ group; $R^{10}$ is an alkyl, aryl or acyl group; and $R^{11}$, $R^{12}$ and $R^{13}$ are independently an optionally substituted alkoxy or alkyl group.

* * * * *